(12) United States Patent
Levy et al.

(10) Patent No.: US 8,109,763 B2
(45) Date of Patent: Feb. 7, 2012

(54) ENDODONTIC FILE

(75) Inventors: Haim Levy, Pardes Hanna (IL); Arie Becker, Kibbutz Afikim (IL); Simon Rothenstein, Rosh HaAyin (IL)

(73) Assignee: Medic.NRG Ltd. (IL)

( * ) Notice: Subject to any disclaimer, the term of this patent is extended or adjusted under 35 U.S.C. 154(b) by 27 days.

(21) Appl. No.: 12/449,681

(22) PCT Filed: Feb. 20, 2008

(86) PCT No.: PCT/IL2008/000221
§ 371 (c)(1),
(2), (4) Date: Oct. 22, 2009

(87) PCT Pub. No.: WO2008/102352
PCT Pub. Date: Aug. 28, 2008

(65) Prior Publication Data
US 2010/0105004 A1    Apr. 29, 2010

(30) Foreign Application Priority Data
Feb. 20, 2007 (IL) .......................... 181439

(51) Int. Cl.
*A61C 5/02* (2006.01)
(52) U.S. Cl. ....................... 433/102; 433/166
(58) Field of Classification Search ............ 433/81, 433/102, 224, 125, 144, 165–166
See application file for complete search history.

(56) References Cited

U.S. PATENT DOCUMENTS

| 2,611,960 | A | * | 9/1952 | Herndon | 433/117 |
| 2,752,682 | A | * | 7/1956 | Wiseman | 433/127 |
| 3,330,040 | A | * | 7/1967 | Kahn | 433/224 |
| 3,906,636 | A | * | 9/1975 | Rainey et al. | 433/102 |
| 4,260,379 | A | | 4/1981 | Groves et al. | |
| 5,533,897 | A | * | 7/1996 | Zdarsky | 433/102 |
| 6,179,617 | B1 | * | 1/2001 | Ruddle | 433/224 |
| 6,431,863 | B1 | * | 8/2002 | Sachdeva et al. | 433/102 |
| 6,443,730 | B2 | * | 9/2002 | Davidson | 433/102 |
| 6,575,748 | B1 | * | 6/2003 | Filhol | 433/102 |
| 6,579,092 | B1 | * | 6/2003 | Senia et al. | 433/102 |
| 6,589,052 | B1 | * | 7/2003 | Wilcko | 433/102 |
| 2003/0017434 | A1 | | 1/2003 | Hagemann | |
| 2006/0127843 | A1 | | 6/2006 | Rosenblood | |
| 2007/0099149 | A1 | | 5/2007 | Levy et al. | |

FOREIGN PATENT DOCUMENTS
WO    WO 00/25698    5/2000
* cited by examiner

*Primary Examiner* — Cris L Rodriguez
*Assistant Examiner* — Hao D Mai
(74) *Attorney, Agent, or Firm* — Karl F. Milde, Jr.; Eckert Seamans; Cherin & Mellott, LLC

(57) ABSTRACT

An endodontic file (2) for use with a dental instrument has at least one cord (6) and a wire (8) wound around at least a major portion of the cord and having an abrasive outer surface (10). A handle having a gripping section is provided for gripping the end of the file and is coupled to the file by a coupler that may be made of a vibration absorbing material.

17 Claims, 3 Drawing Sheets

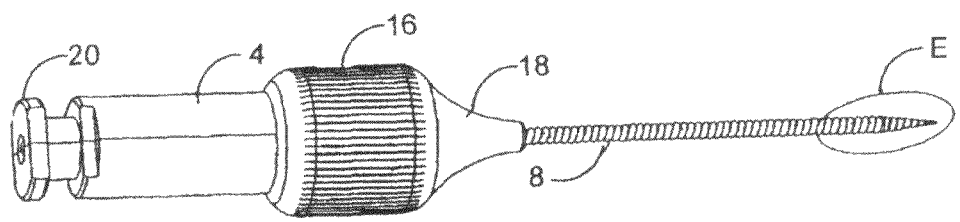
FIG. 1
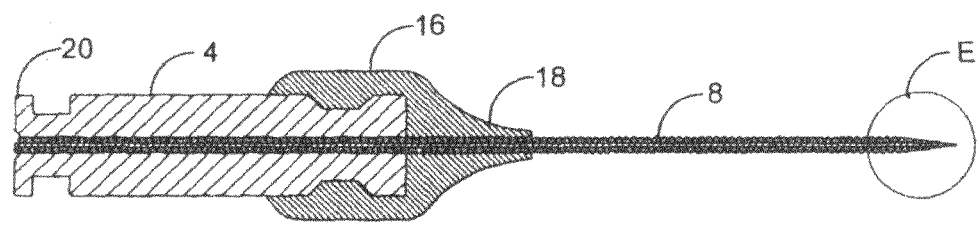
FIG. 2
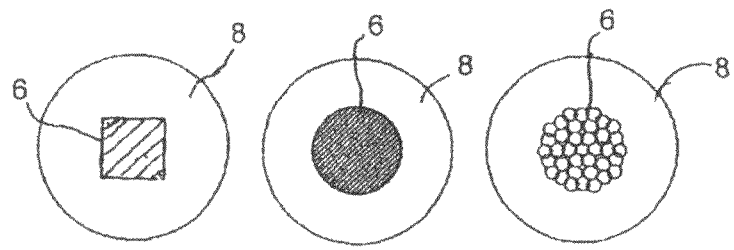
FIG. 3C   FIG. 3B   FIG. 3A
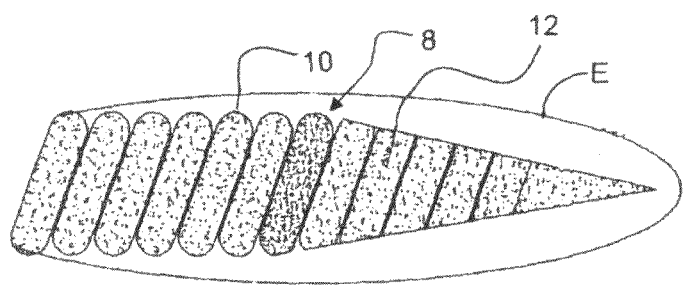
FIG. 4

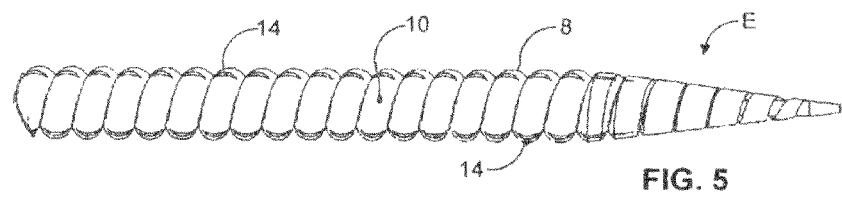
FIG. 5
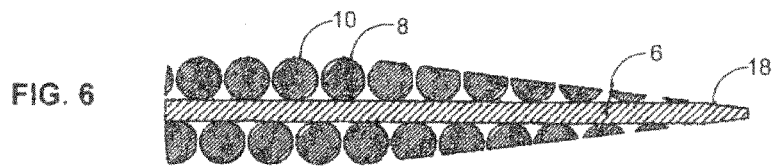
FIG. 6
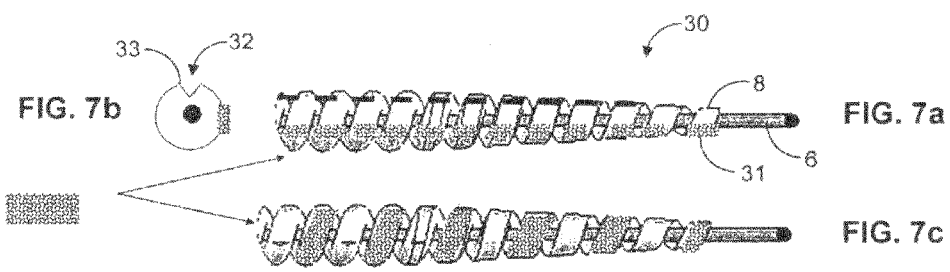
FIG. 7b  FIG. 7a
FIG. 7c
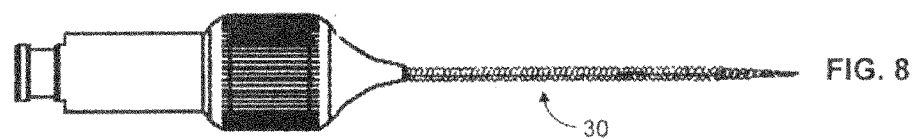
FIG. 8
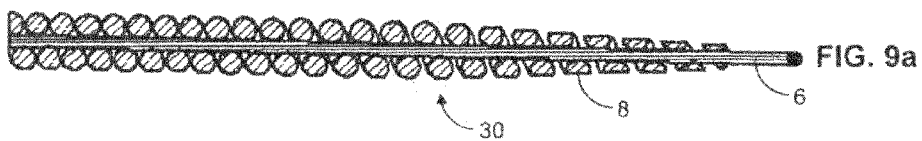
FIG. 9a

ENDODONTIC FILE

FIELD OF THE INVENTION

The present invention relates to endodontic devices and more particularly to an endodontic file to be utilized with a dental instrument.

BACKGROUND OF THE INVENTION

US20070099149 entitled "Endodontic device and method of utilizing and manufacturing same" in the name of the present applicant discloses an endodontic device for cleaning, filing or reaming root canals. The device includes one or more metallic, flexible strands having an edge, a working section, a connecting section and a coupling head connected thereto. The strands are coated along the working section with a thin layer of a binder having abrasive particles embedded therein. In the file disclosed by US20070099149 the flexible, longitudinal strands are so constructed that their outer surfaces serve as active filing surfaces. The whole contents of US20070099149 are incorporated herein by reference.

SUMMARY OF THE INVENTION

In accordance with the invention there is therefore provided an endodontic file to be utilized with a dental instrument, said endodontic file comprising at least one cord and a wire wound around at least a major portion of the cord, said wire having an abrasive outer surface.

The structure of the file according to the present invention, renders the file to be flexible almost diminishing its longitudinal rigidity or stability. This characteristic dictates the manner of its use, namely, the manner of introducing the file into a root canal of a tooth to be treated. Whereas the prior art files are inserted into a root canal by pushing the file axially into the root canal, the file according to the present invention is inserted by imparting a rotational movement thereto. When the leading end of the file approaches the apex of the root canal, the file will be caught by the narrow walls of the canal, preventing further penetration, thereby protecting the apex tissue from being contacted and injured by the penetration of the file member beyond the root canal.

Owing to the substantial flexibility of the file according to the present invention, the file is effective in cleaning convoluted root canals since it merely closely follows the canal's contours without injuring the dentine layer.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 is an isometric view of an endodontic file, according to an embodiment of the present invention;

FIG. 2 is cross-sectional view of the file, according to an embodiment of the present invention;

FIGS. 3A, 3B and 3C are cross-sectional views of various configurations of a cord that is wound around a central core cable of the file;

FIG. 4 is an enlarged isometric view of an end portion of the file shown in FIG. 1;

FIG. 5 is an enlarged view of a file showing serrations;

FIG. 6 is an enlarged cross-sectional view of the end portion of the file shown in FIG. 2

FIGS. 7a, 7b and 7c are pictorial representations showing a detail of a working section of a file according to alternative embodiments of the invention;

FIG. 8 is a pictorial representation showing a detail of a working section of a file having an intermittent textured coating;

FIGS. 9a and 9b are pictorial representations showing respectively a longitudinal cross-section and an outer elevation of a working section of a file having a multi-strand flexible core cable;

Figure 9B:

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF EMBODIMENTS

In the following description of some embodiments, identical components that appear in more than one figure or that share similar functionality will be referenced by identical reference symbols.

FIGS. 1 and 2 show an endodontic file 2 to be utilized with a dental instrument, such as a file handle 4 and/or a hand piece such as a dentist's drill (not shown), to which the handle 4 is releasably attachable. The file 2 is composed of a cord 6 and a wire or twined wire 8, closely or loosely wound around the cord 6. The cord 6 may consist of a cable made of twisted strands, as shown in FIGS. 3A and 6, of a single wire, e.g., a stainless-steel wire, circular in cross-section (FIG. 3B) or, multilateral in cross-section (FIG. 3C). Around the cord cable 6, there is wound a wire or twined wire 8, e.g., that may be made of stainless-steel, having a diameter of 0.2-0.3 mm, rendering the cord 6 flexible and durable during use. The outer surface 10 of the wound or twined wire 8 is roughened forming an abrasive surface (FIG. 4). The roughening, essentially forming tiny depressions and/or projections 12, may be configured as grooves or serrations 14 (FIG. 5), slits, scratches, or the like, extending longitudinally, and/or diagonally across the wire 8. Alternatively, the roughening may be performed by sandblasting or by other processes. Such a process can advantageously be achieved using the process described in above-mentioned US20070099149, wherein the outer surface 10 of the wire 8 is coated with an abrasive layer. The abrasive layer may be composed of a binder, e.g., a thin nickel binder containing abrasive particles, e.g., particles selected from the group including aluminum oxide, silicon carbide, zirconium or diamond powder. When a twined wire 8 is used, the outer surface 10 need not necessarily be further roughened, since the twining itself provides diagonally-extending grooves which, during use, provide abrasive action. A cross-section of the file is advantageously tapered so as to form a narrow end portion E. Additionally or alternatively, the end portion E may be pointed, e.g. by grinding or otherwise sharpening, facilitating ease of penetration into the root canal of a tooth. Optionally, the end portion E as well as the other effective portion of the file, may be thinly coated with gold.

As further seen in FIGS. 1 and 2, the file 2 is attached to a handle 4 by any known technique, and advantageously, there is applied a coupler 16 made with vibration-absorbing materials having a tapered nose 18 constituting a gripping section for gripping a portion of the file 2. A similar arrangement is described in US20070099149.

The handle 4 may also be formed with a head section 20 configured to be releasably attached to an endodontic hand piece for imparting rotational movement to the file.

FIGS. 7a, 7b and 7c are pictorial representations showing a detail of a working section 30 of a file according to alternative embodiments of the invention. In FIG. 7a the working section 30 comprises a single-strand central cord 6 around which is wound a spiral of wire 8 having a textured coating 31 along at least part of its surface. FIG. 7b shows an end elevation of the working section 30 of the file showing a vertical notch or groove that is cut into an outer surface of the wire 8, thereby forming inclined V-shaped surfaces whose edges 33 may be sharpened to serve as cutting tool. In FIG. 7c, an intermittent spiral coating is used so as to cover alternate spirals.

FIG. 8 is a pictorial representation showing a detail of the working section 30, an end portion of which has an intermittent textured coating according to any of the embodiments shown in FIGS. 7a to 7c.

FIGS. 9a and 9b are pictorial representations showing respectively a longitudinal cross-section and an outer elevation of a working section 30 of a file whose cord 4 is formed of a multi-strand flexible core cable around which is wound a spiral wire 8 according to any of the embodiments described above. A free end of the core cable having a length of between 2 to 4 mm remains uncovered and is laser treated to form a globule 35 that is used as a pathfinder when cutting its way through a root canal.

Figure 10A:
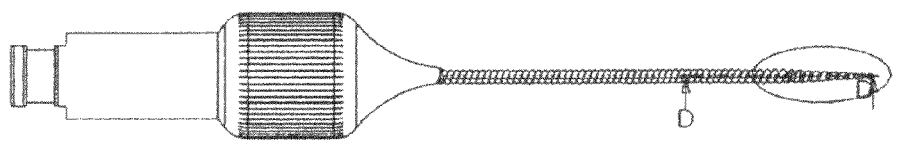
FIGS. 10a and 10b are pictorial representations showing a detail of a working section of a file according to alternative embodiments of the invention.
Figure 10B:

FIGS. 10a and 10b are pictorial representations showing a detail of a working section of a file whose outer spiral 8 is wound with varying pitch. Thus, it is seen that at the rear end shown as D, which is attached to the dentist's drill or hand piece, adjacent spirals are close together while toward the working end shown as B they are further apart.

Figure 11A:
FIGS. 11a, 11b, 11c and 11d are pictorial representations showing a detail of a working section of a file according to alternative embodiments of the invention.
Figure 11B:
Figure 11C:
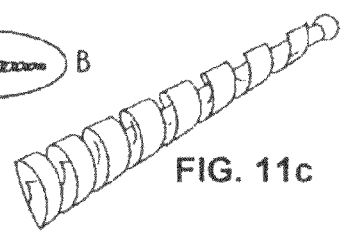
Figure 11D:
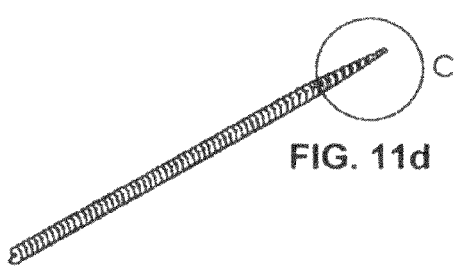

FIGS. 11a, 11b, 11c and 11d are pictorial representations showing a detail of a working section shown in FIG. 11b as B and in FIG. 11d as C of a file whose spirals are formed with varying pitch similar to the embodiments shown in FIGS. 10a and 10b.

It will be evident to those skilled in the art that the invention is not limited to the details of the foregoing illustrated embodiments and that the present invention may be embodied in other specific forms without departing from the essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

There has thus been shown and described a novel endodontic file which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. An endodontic file to be utilized with a dental instrument, said endodontic file comprising:
   at least one flexible cord and a wire having an abrasive outer surface wound around at least a major portion of the cord to form a spiral having multiple turns of wire,
   a handle having an axial bore for gripping the at least one cord and having at a first end thereof a gripping section for fixedly coupling to a rotatable mount in the dental instrument such that the flexible cord extends from the gripping section to a working section of the endodontic file, and
   a vibration absorber mounted over a second end of the handle opposite the first end so as to directly cover a portion of the cord protruding from the second end of the handle.

2. The endodontic file as claimed in claim 1, wherein the abrasive outer surface of the wire is coated with a binder containing abrasive particles selected from the group including aluminum oxide, silicon carbide, zirconium or diamond powder.

3. The endodontic file as claimed in claim 1, wherein an end portion is pointed.

4. The endodontic file as claimed in claim 1, wherein said cord is constituted by a plurality of threads.

5. The endodontic file as claimed in claim 4, wherein said threads are twisted.

6. The endodontic file as claimed claim 1, wherein said cord is round in cross-section.

7. The endodontic file as claimed in claim 1, wherein said cord is multilateral in cross-section.

8. The endodontic file according to claim 1, wherein the dental instrument is an endodontic hand piece and said handle includes a head section configured to be releasably attached to the endodontic hand piece.

9. The endodontic file according to claim 1, wherein at least part of the abrasive outer surface has a textured coating.

10. The endodontic file according to claim 9, having a vertical notch or groove cut into an outer surface of the wire to form inclined V-shaped surfaces.

11. The endodontic file according to claim 10, wherein edges of the V-shaped surfaces are sharpened to serve as cutting tool.

12. The endodontic file according claim 1, having an intermittent coating to cover alternate turns of the spiral.

13. The endodontic file according to claim 1, wherein the cord is formed of a multi-strand flexible core cable.

14. The endodontic file according to claim 1, wherein the cord is formed of a single-strand flexible core cable.

15. The endodontic file according to claim 1, wherein a free end of the flexible cord remains uncovered and is laser treated to form a globule.

16. The endodontic file according to claim 1, wherein the spiral is wound with varying pitch.

17. The endodontic file according to claim 1, wherein the spiral is wound with wire having a diameter of 0.2-0.3 mm.

* * * * *